United States Patent
Schmieding

(10) Patent No.: US 6,623,524 B2
(45) Date of Patent: Sep. 23, 2003

(54) METHOD FOR ANTERIOR CRUCIATE LIGAMENT RECONSTRUCTION USING CROSS-PIN IMPLANT WITH EYELET

(75) Inventor: Reinhold Schmieding, Naples, FL (US)

(73) Assignee: Arthrex, Inc., Naples, FL (US)

( * ) Notice: Subject to any disclaimer, the term of this patent is extended or adjusted under 35 U.S.C. 154(b) by 67 days.

(21) Appl. No.: 09/875,970

(22) Filed: Jun. 8, 2001

(65) Prior Publication Data
US 2001/0053934 A1 Dec. 20, 2001

Related U.S. Application Data
(60) Provisional application No. 60/210,472, filed on Jun. 9, 2000.

(51) Int. Cl.[7] ............................................. A61F 2/08
(52) U.S. Cl. ................................ 623/13.14; 128/898
(58) Field of Search .......................... 623/11.11, 13.11, 623/13.12, 13.13, 13.14, 13.19, 13.2, 20.14; 606/72, 96, 98, 99; 128/898

(56) References Cited

U.S. PATENT DOCUMENTS

| | | |
|---|---|---|
| 4,985,032 A | 1/1991 | Goble |
| 5,098,435 A | 3/1992 | Stednitz et al. |
| 5,266,075 A | 11/1993 | Clark et al. |
| 5,350,380 A | 9/1994 | Goble et al. |
| 5,354,300 A | 10/1994 | Goble et al. |
| 5,356,413 A | 10/1994 | Martins et al. |
| 5,393,302 A | 2/1995 | Clark et al. |
| 5,397,356 A | 3/1995 | Goble et al. |
| 5,423,823 A | 6/1995 | Schmieding |
| 5,431,651 A | 7/1995 | Goble |
| 5,562,671 A | 10/1996 | Goble et al. |
| 5,601,562 A | 2/1997 | Wolf et al. |
| 5,918,604 A | 7/1999 | Whelan |
| 5,961,538 A * | 10/1999 | Pedlick et al. ............... 606/232 |
| 6,045,554 A * | 4/2000 | Grooms et al. ............... 606/73 |
| 6,090,998 A * | 7/2000 | Grooms et al. ............. 128/898 |
| 6,099,529 A * | 8/2000 | Gertzman et al. ............. 606/72 |
| 6,132,433 A | 10/2000 | Whelan |
| 6,152,928 A * | 11/2000 | Wenstrom, Jr. ............. 606/151 |

FOREIGN PATENT DOCUMENTS

FR 2684543 6/1993

OTHER PUBLICATIONS

C. Harner, et al., "Anterior Cruciate Ligament Reconstruction: Endoscopic Versus Two–Incision Technique", Arthroscopy: vol. 10, No. 5, pp. 502–512 (1994).

B. Shaffer, et al., "Graft–Tunnel Mismatch in Endoscopic Anterior Cruciate Ligament Reconstruction: A New Technique of Intraarticular Measurement and Modified Graft Harvesting", Arthroscopy: vol. 9, No. 6, pp. 633–646 (1993).

(List continued on next page.)

Primary Examiner—Justine R. Yu
(74) Attorney, Agent, or Firm—Dickstein Shapiro Morin & Oshinsky, LLP

(57) ABSTRACT

A surgical implant for securing ligament grafts into a joint. The implant is formed entirely of allograft cortical bone, and has a tapered tip with a suture eye. A length of suture is knotted or looped through the eye. The suture is used to draw the implant transversely through a looped graft construct to fix the graft by spanning a bone socket, for example. In a preferred embodiment, the implant is used for knee ligament repair by forming a longitudinal socket in a bone. A flexible strand is drawn with the pin through the bone. A looped portion of the flexible strand is diverted so as to protrude out of the entrance to the longitudinal socket. The ends of the flexible strand remain accessible on either side of the bone. The ligament graft is captured within the strand loop protruding from the entrance to the socket. The strand is retracted into the socket, drawing the graft into the socket by pulling on the accessible ends of the flexible strand. The graft is fixed in the socket using the transverse implant.

22 Claims, 8 Drawing Sheets

OTHER PUBLICATIONS

P. Scranton, Jr., et al., "Outpatient Endoscopic Quadruple Hamstring Anterior Cruciate Ligament Reconstruction", Operative Techniques in Orthopaedics, pp. 177–180 (1996).

K. Leeds, "Arthroscopic Reconstruction of the ACL With Artificial Ligament", Arthroscopy, vol. 12, No. 1, pp. 65–68 (1987).

R. Larson, "Anterior Cruciate Ligament Reconstruction with Hamstring Tendons", Operative Techniques in Orthopaedics, vol. 6, No. 3, pp. 138–141 (Jul. 1996).

R. Scherer, et al., "Investment Opportunities in Orthopedics", Orthopedic Industry Overview, (Aug. 1998).

S. Howell, "ACL Reconstruction Bone Mulch Screw WasherLoc", pp. 1–14 Arthrotek (1998).

D. McKernan, "Surgical Technique for Mitek RIGIDfix ACL Reconstruction", pp. 1–6, Mitek Products (1999).

T. Rosenberg, "Technique for ACL Reconstruction With Acufex Director Drill Guide and Endobutton CL", Smith & Nephew (1999).

F. Noyes, et al., "PCL Reconstruction With the Acufex Director Drill Guide Using the Noyes All–Inside PCL Technique and a Double Bundle Quadriceps Tendon Graft".

R. Hunter, "Quadruple Loop Hamstring Graft Surgical Technique With the Phantom SoftThread Interference Screw", Dpuy OrthoTechnology (1998).

L. Paulos, "Endoscopic Anterior Cruciate Ligament Reconstruction", pp. 1–14, Mitek Products, Inc. (1994).

* cited by examiner

METHOD FOR ANTERIOR CRUCIATE LIGAMENT RECONSTRUCTION USING CROSS-PIN IMPLANT WITH EYELET

This application claims the benefit of U.S. provisional application Ser. No. 60/210,472, filed Jun. 9, 2000.

BACKGROUND OF THE INVENTION

1. Field of the Invention

The present invention relates to a method of anterior cruciate ligament (ACL) reconstruction and, more specifically, to a method a ACL reconstruction using a pin formed of allograft bone material.

2. Description of the Related Art

When a ligament or tendon becomes detached from associated bone, surgery usually is required to re-secure the ligament or tendon. Often, a substitute ligament, or graft, is attached to the bone to facilitate re-growth and permanent attachment. Various methods of ligament graft attachment are known, including staples, suture over buttons, and interference screw fixation.

Staples and suture buttons are disadvantageous because they often do not provide fixation sufficient to withstand the normal tensile loads. With suture button fixation, for example, a strand of suture couples the button and the substitute ligament. This strand becomes the "weakest link in the chain," and if the strand breaks, the ligament detaches.

A stronger graft attachment can be obtained by interference screw fixation. An interference screw is used to wedge a graft bone block to the wall of a graft tunnel. See, e.g., U.S. Pat. Nos. 5,211,647, and 5,603,716, incorporated herein by reference. Although interference screw attachment is more secure than using staples or suture buttons, it is sometimes neither possible nor desirable to provide such fixation, particularly in the femoral tunnel. In revision situations, for example, where a previous reconstruction has been performed, placing a second femoral tunnel close to the previous tunnel may not be indicated.

In other cases, a semitendinosus graft must be used because the previous reconstruction used the mid third patellar tendon. Although a bone-semitendinosus graft-bone construct may be prepared using a workstation as disclosed in U.S. Pat. No. 5,397,357, the procedure is time consuming, and may be undesirable for other reasons.

A fixation technique which provides strong attachment of a semitendinosus graft in the femoral tunnel, using a transverse pin, is disclosed in U.S. Pat. No. 5,601,562, of common assignment with the present application. The transverse pin is inserted through a loop in a tendon graft. A threaded portion of the pin screws into the bone as the pin is advanced with rotation into the repair site. The technique is disadvantageous, however, because the graft can wrap around the pin as it is rotated. An improved tendon loading technique is the subject of U.S. Pat. Nos. 5,918,604 issued Jul. 6, 1999 and 6,132,433 issued Oct. 17, 2000.

An implant with back-biting threads has been developed as disclosed in U.S. Pat. No. 5,895,425 issued Apr. 20, 1999, also incorporated in its entirety herein by reference. The implant can be installed by impaction and so overcomes the graft-wrapping problem.

The need exists for methods of tendon repair that utilize surgical implants made of biologically-derived materials, such as allograft bone material, whereby biologic implants can be installed as transverse pins and can support tendon grafts.

SUMMARY OF THE INVENTION

The present invention overcomes the problems of the prior art and fulfills needs such as those noted above by providing a surgical bone implant made of allograft (or synthetic) bone. The implant preferably is formed of allograft cortical bone, and has a tapered tip with an eye for receiving suture. The implant can be advanced into bone by impaction. The implant is useful for various surgical indications, including fixating tendon grafts in a joint using the implant in a transverse, intraosseous application. Preferably, a looped graft is fixed in a bone socket by inserting the implant through the loop in the graft. The implant spans the bone socket clearance and is supported by the side walls that bound the socket opening.

The bone implant has a shaft with distal and proximal ends. For ease of insertion, the tip of the shaft is tapered. The remainder of the shaft is smooth and cylindrical. An eye for attachment of a suture is provided on the tip, preferably in the form of a 2 mm hole drilled through the tip. Suture is used to pull the implant into position. Axial grooves are formed on either side of the tip and intersect with the suture eye to provide clearances for a length of suture looped or knotted through the eye. Accordingly, the suture will not bind in the bone openings as the implant is urged into position.

The preferred implant is 5 cm long and is about 3–5 mm in diameter. The implant is of sufficient flexural strength and/or toughness to support a tendon graft loop using the implant installed as a transverse pin.

As applied in the knee, a method of using the implant includes the use of standard techniques to drill a longitudinal tunnel in the tibia. Subsequently, a femoral socket is formed, preferably in the lateral femoral condyle. According to the present invention, forming the socket is preferred to forming a tunnel through the lateral femoral cortex. Advantageously, the diameters of the tibial tunnel and femoral socket are made just large enough to accommodate the graft in a snug fit.

A tunnel hook, mounted on a cross-pin drill guide, is inserted through the tibial tunnel and into the femoral socket. A drill pin directed by the drill guide is drilled through the femur to intersect the femoral socket. The drill pin passes through the capture slot of the tunnel hook.

A hole then is formed in the femur, preferably using a cannulated drill placed over the guide pin, to accommodate the transtibial implant. Preferably the diameter of the hole is such that the pin will fit snugly in the hole.

Next, a flexible strand, preferably a wire formed of nitinol, is attached to the guide pin and pulled transversely across the femur, a portion of the strand passing through the capture slot of the tunnel hook. The ends of the strand protrude from the medial and lateral sides of the femoral shaft. With the strand ends secured to prevent accidental pull-out, the tunnel hook is withdrawn axially from the femoral tunnel, the strand being captured in the slot of the hook to form a strand loop that is pulled through of the socket and into the tunnel.

The hook is retracted completely, through the femoral socket and out of the tibial tunnel, such that a loop of the flexible strand protrudes from the entrance to the tunnel. Free ends of the strand remain exposed on either side of the femoral shaft.

The graft is passed through the diverted loop of the flexible strand. The loop is retracted into the femoral socket by pulling evenly on the medial and lateral ends of the strand. As a result, the graft is drawn into the socket.

A length of suture is attached at one end to the flexible strand and at the other end to the implant. The flexible strand is used to draw the suture into the femur. Additionally, the implant also can be impact driven into place. The implant passes under the tendon across the femoral socket, and coming to rest with either end of the implant supported in the femoral bone, thus securing the graft in the femoral socket.

Tibial fixation of the graft can be performed by various known methods, including interference screw fixation, which provides the most secure post-operative result; distal fixation with a cancellous screw using a post and washer technique; and a belt buckle staple technique utilizing a pair of ligament staples. As a further alternative, tibial fixation is achieved by way of the transverse pin implant described above for the femur, and femoral fixation is by one of the other known methods.

An alternative method of tendon loading is also provided for a closed-loop graft reconstruction. According to the alternative method, a flexible line is joined to one end of the strand. A strand/line loop is formed so as to protrude from the entrance to the tibial tunnel and present the junction between the strand and the line. The strand and the line are dejoined, opening the strand/line loop to accept the graft. The strand and line are rejoined so as to capture the graft, and the procedure continues substantially as set forth above.

Other features and advantages of the present invention will become apparent from the following description of the invention which refers to the accompanying drawings. For example, although the description herein relates to ACL grafts and forming femoral tunnels in the knee, it will become apparent that expanded indications for the inventive method include other joints and replacement of other ligament or tendon structures using various types of graft constructs.

DETAILED DESCRIPTION OF THE PREFERRED EMBODIMENTS

Figure 7A:
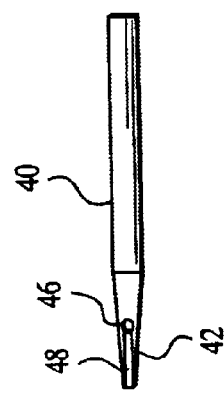
FIG. 7A illustrates a transverse allograft bone implant according to the present invention.
Figure 7B:
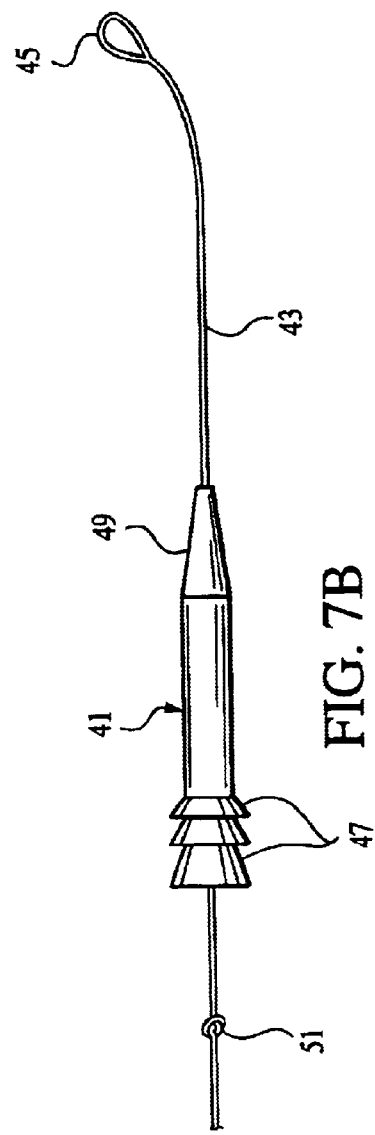
FIG. 7B illustrates a transverse synthetic implant according to the present invention.

The implant of the present invention will be described in conjunction with a surgical method utilizing preferred embodiments of implants 40 and 41, which are shown in FIGS. 7A and 7B, respectively.

Figure 2:
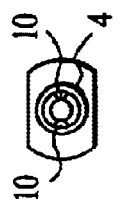
FIG. 2 is a distal end view of the tunnel hook of FIG. 1.
Figure 1:
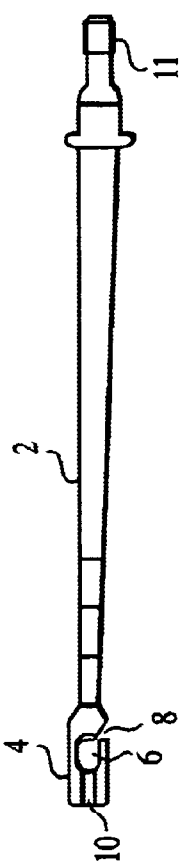
FIG. 1 is an elevation of a tunnel hook according to the present invention.

Referring initially to FIGS. 1 and 2, the present invention involves the use of a slim, longitudinal tunnel hook 2, which includes a shaft having a distal end and a proximal end. The distal end of tunnel hook 2 is provided with a hook 4, having a capture slot 6.

Various features of tunnel hook 2 are provided for ease of use in the inventive procedure of the present invention. The purpose of the following features will become more clear in light of the method described below. Angled opening 8 allows escape of a graft-passing wire from capture slot 6. Channels 10 on either side of hook 4 accommodate portions of the graft-passing wire as it forms a loop through the femoral tunnel. The proximal end of tunnel hook 2 features a mounting flange 11 for engagement with a drill guide.

Figure 3:
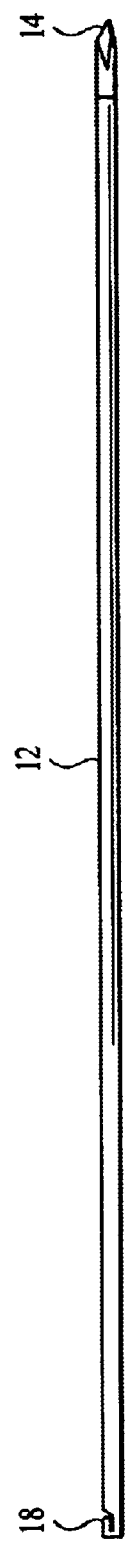
FIG. 3 is an elevation of a drill pin according to the present invention.
Figure 5:
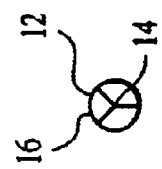
FIG. 5 is a distal end view of the drill pin of FIGS. 3 and 4.
Figure 4:
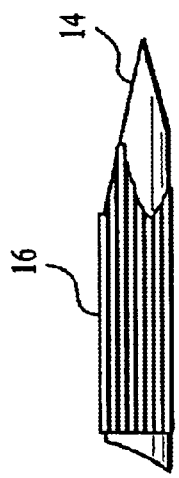
FIG. 4 is an enlarged view of the distal tip of the drill pin of FIG. 3.

Referring to FIGS. 3, 4, and 5, the invention also involves the use of a drill pin 12, which includes an elongated, narrow shaft having a pointed distal end and a proximal end. The distal end of drill pin 12 is provided with a sharp, trocar tip 14 and a fluted drilling region 16 disposed adjacent to and proximal the faces of trocar tip 14. The proximal end of drill pin 12 includes a hook 18 having an angled opening into its capture slot for engaging the graft-passing wire, as described more fully below.

Figure 6:
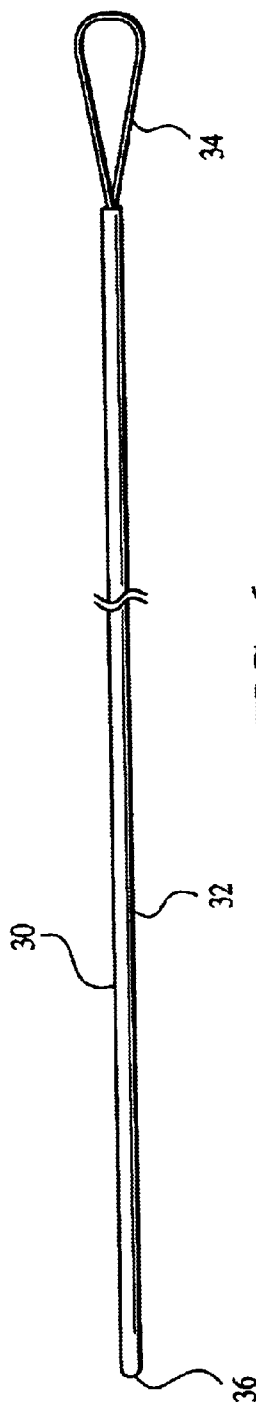
FIG. 6 illustrates a graft-passing wire according to the present invention.

Referring to FIG. 6, a nitinol graft-passing wire 30 is shown. Graft-passing wire 30 includes a flexible portion 32 having a loop 34 formed on the distal end and a rounded proximal end 36.

FIG. 7A illustrates transverse implant 40. Implant 40 has a blunt proximal end and a tapered distal end 42, for ease of insertion. A suture eye 46 is formed in the distal end. Axial channels or grooves 48 are formed on either side of the tapered tip 42 to provide relief for a length of suture that is knotted or looped through eye 46. Accordingly, the suture will not bind in the bone openings as the implant is urged into position. Eye 46 is provided in the form of a 2 mm hole drilled through the tip. The suture is used to draw the implant into a bone hole, as described further below. The remainder of the shaft is smooth and cylindrical.

The preferred implant is 5 cm long and is about 3–5 mm in diameter. The implant is of sufficient flexural strength and/or toughness to support a tendon graft loop using the implant installed as a transverse pin.

Implant 40 can be machined from allograft cortical bone using known techniques, and preferably is made from a single piece of material. Allograft material preferably is freeze-dried cortical bone. Alternatively, the implant can be made of a synthetic material, preferably a synthetic cortical bone material. A preferred synthetic bone material is made up of either tricalcium phosphate (TCP) or hydroxyapatite (HA), combined with a biodegradable polymer, preferably a polylactide, such as PLA.

Referring to FIG. 7B, an alternative embodiment of an implant 41 according to the present invention is shown. Implant 41 has an integrated guide wire 43 for drawing the implant into a bone hole, as described below in connection with implant 40. The integrated guide wire 43 has a loop 45 for passing the guide wire through bone. The guide wire is prevented from pulling through the implant by way of a knot 51, for example, formed in the wire. Alternatives to knot 51 include a crimp, swage, or bead, for example. A blunt proximal end is provided with ridges 47 to enhance mechanical fixation on bone. A tapered distal end 49 eases insertion. The remainder of the shaft preferably is smooth and cylindrical.

Figure 8:
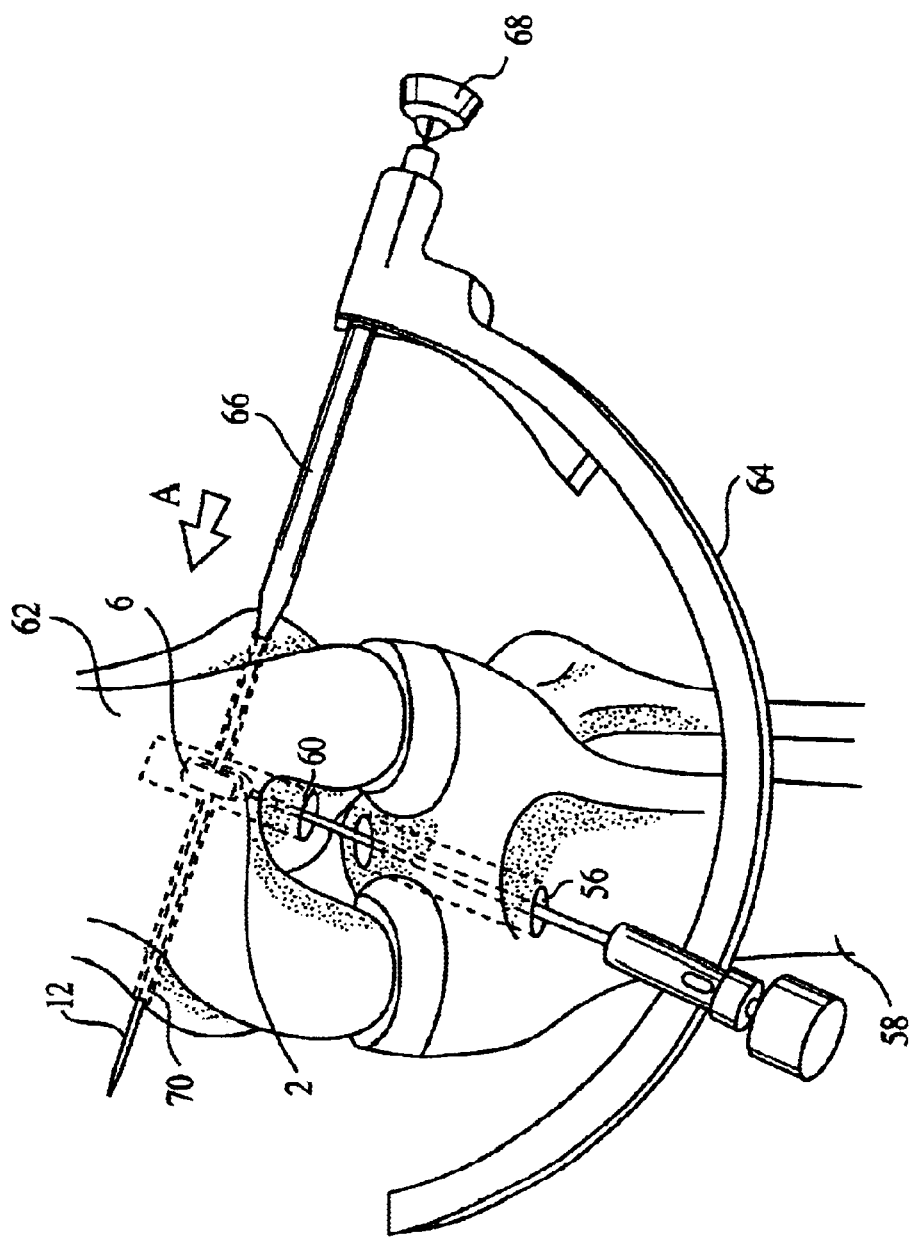
FIG. 8 is a schematic view of a hook and a drill pin mounted on a drill guide and disposed within the femoral socket according to the present invention.

The method of the present invention is described with reference to FIGS. 8 through 14. A longitudinal tibial tunnel 56 is formed using known techniques of drilling up through the tibia 58, as shown in FIG. 8. Reproducible tunnel placement is achieved using instruments that reference intra-articular anatomical constants. A cannulated drill, received over a guide, is used to drill the tibial tunnel. Depending on the size of the graft, tunnel diameters of 7, 8, 9, and 10 mm typically are used.

Once tibial tunnel 56 is formed, a cannulated headed reamer is used to provide a closed-ended socket 60 in the femur 62. The socket is formed to a minimum depth of about 40 mm to accommodate the insertion depth of tunnel hook 2. The knee should be placed in 90° of flexion when forming the tibial tunnel and femoral socket.

The tunnel and socket can be modified in various ways using tunnel taps. For example, crenulations formed in the tibial tunnel provide additional friction and help eliminate unwanted graft rotation during interference screw insertion. A spiral groove formed in the tunnel wall provides additional interference friction of the graft collagen against the compressed cancellous bone in the tunnel. A rasp may be used to create an oval-shaped tunnel and femoral socket to accommodate insertion of four tendon strands.

After the tibial tunnel and femoral socket are complete, tunnel hook 2, fitted onto a C-ring cross-pin drill guide 64, is inserted through tibial tunnel 56 and into femoral socket 60. Tunnel hook 2 will capture within slot 6 a graft-passing wire 30 used in loading the graft tendons into the femoral socket, as described below with respect to FIGS. 12 and 13.

Referring again to FIG. 8, with tunnel hook 2 and drill guide 64 in place, a 2 mm drill pin sleeve 66 is advanced in the direction of arrow A up to the skin proximal to the femoral condoyle to indicate an incision site. The drill guide is positioned to allow the pin to pass parallel to the coronal plane, without excessive posterior or anterior divergence. A 2-cm incision is made transversely at this site through the skin and fascia lata, and soft tissue is cleared down to the condoyle.

Drill pin sleeve 66 is advanced until it contacts bone. Over-tightening of the drill pin sleeve against the femoral cortex is avoided to prevent the drill pin alignment from deviating and missing capture slot 6 of tunnel hook 2. A depth indicator on the sleeve is used to gauge the length of implant 40 that will be required.

With the sleeve in position against the cortical bone, drill pin 12, 2 mm. in diameter, is chucked into a power drill, and advanced with rotation through the femur until it exits the skin on the medial side 70. To ensure that the drill pin passes within the capture slot 6 of tunnel hook 2, torque on the drill guide and changes in knee flexion are avoided during drilling.

Figure 9:
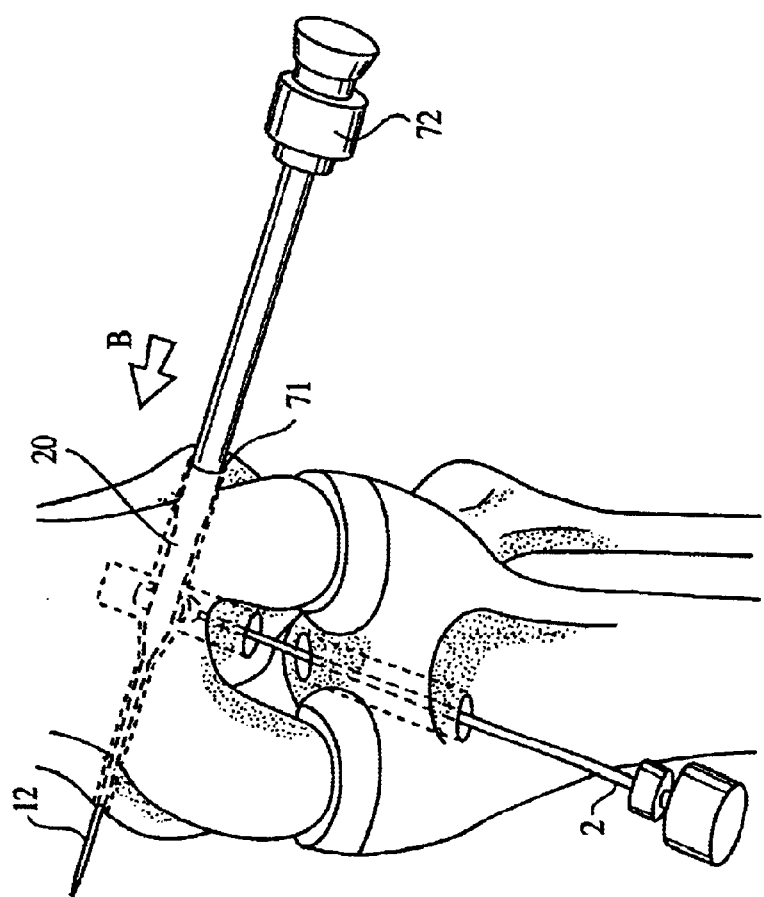
FIG. 9 is a schematic illustration of the formation of a transverse femoral hole for the transverse implant according to the present invention.

Referring to FIG. 9, C-ring cross-pin drill guide 64 is removed, and a cannulated drill is placed over the guide pin and driven with rotation in the direction of arrow B to provide a hole 71 to accommodate implant 40. Hole 71 also can be formed using reamers, as well as other methods known in the art. For example, the drill may be replaced with a tunnel dilator 20 to form a channel in the femur for the remainder of implant 40. Tunnel dilator 20 is mounted on a driver/extractor 72 and driven with a mallet in the direction of arrow B up to the depth stop (not shown).

Figure 10:
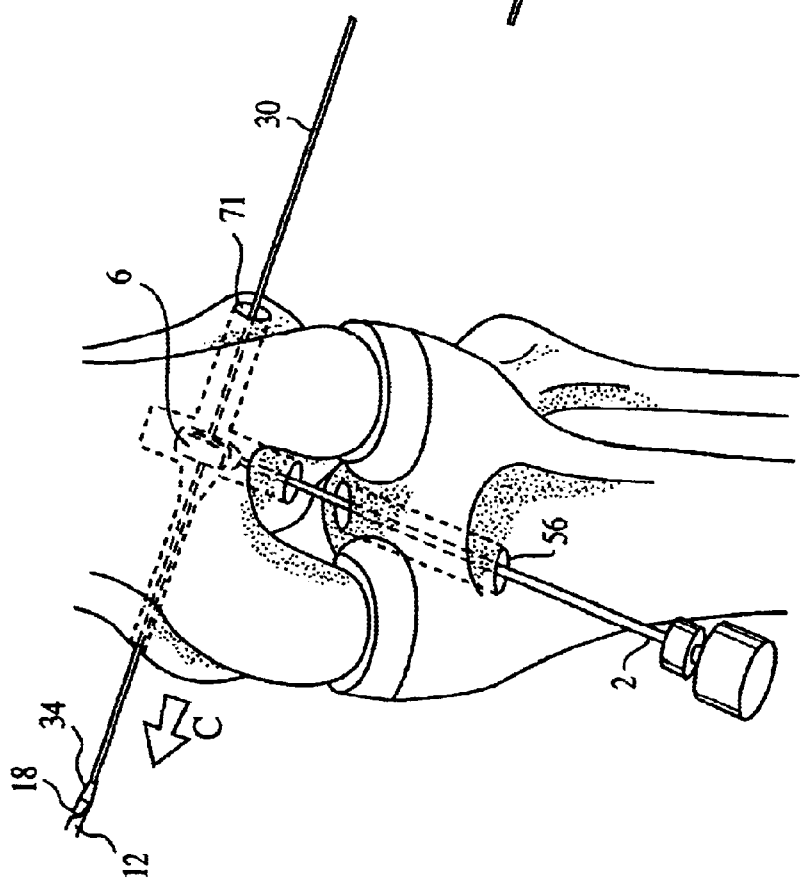
FIG. 10 illustrates a flexible strand attached to the drill pin and being pulled through the femur according to the present invention.

Referring to FIG. 10, once the hole has been formed, loop 34 of nitinol graft-passing wire 30 is hooked onto hook 18 on the proximal end of drill pin 12. By pulling on the drill pin in the direction of arrow C, the graft-passing wire is drawn transversely across the femur through capture slot 6 until it is positioned with lengths at either end protruding from the medial and lateral sides of the femoral shaft. Hemostats 74 (FIG. 12) are clipped onto the ends of the wire to prevent them from being pulled into the transverse femoral tunnel 70.

Figure 11:
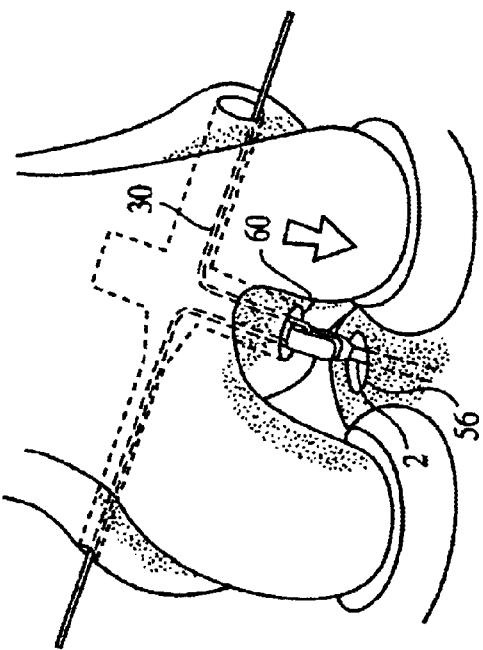
FIG. 11 illustrates a loop of the flexible strand being pulled by the hook and out through the femoral socket according to the present invention.
Figure 12:
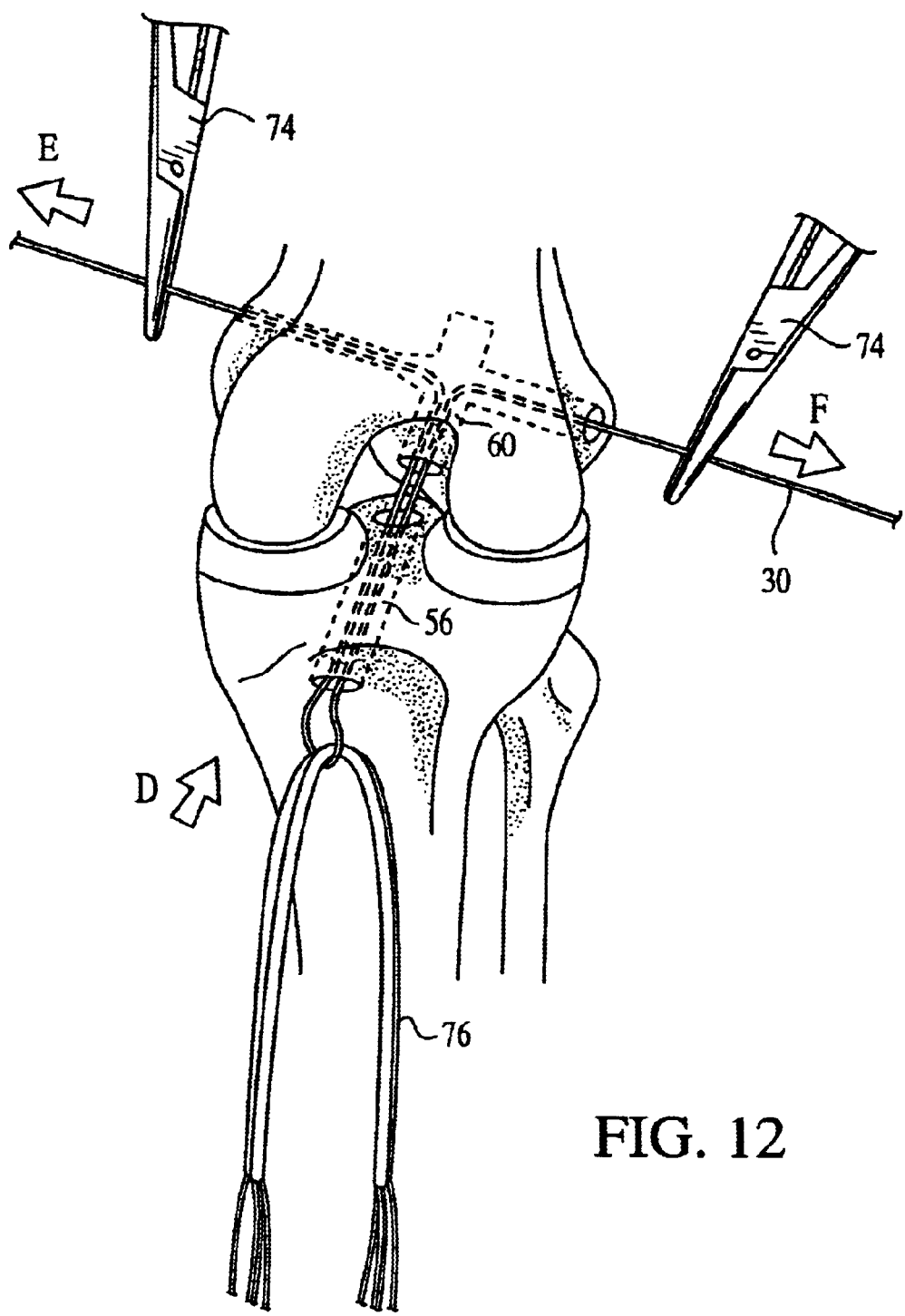
FIG. 12 illustrates the flexible strand loop having been diverted through the tibial tunnel, capturing a ligament graft, and pulling the graft into the tibial tunnel according to the present invention.

Referring to FIGS. 11 and 12, once graft-passing wire 30 has been positioned across the femur, tunnel hook 2 is retracted longitudinally from femoral socket 60 and tibial tunnel 56, and in the process draws graft-passing wire 30 captured in slot 6 to form a loop in the wire that protrudes from the entrance of tibial tunnel 56 on the anterior tibial cortex. As shown in FIG. 12, the semitendinosus and gracilis tendons 76 are placed evenly over the wire loop. The loop containing the tendons is retracted in the direction of arrow D back through the tibial tunnel and into the femoral socket by pulling evenly on the medial and lateral ends of the graft-passing wire, as shown by arrows E and F, respectively. Twisting of the graft during insertion is avoided.

Figure 13:
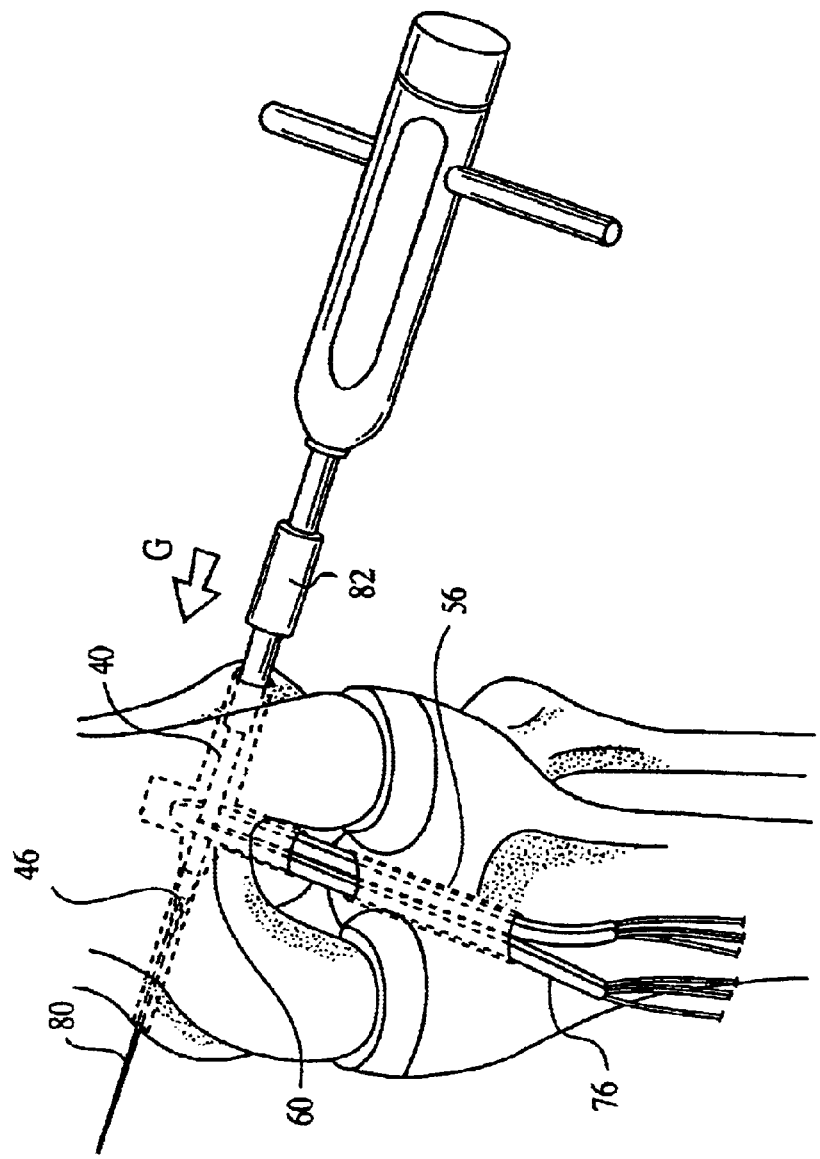
FIG. 13 illustrates the ligament graft, having been loaded through the longitudinal tibial tunnel and into the femoral socket, being fixated using a transverse pin according to the present invention.

Referring to FIG. 13, once the tendon graft 76 has been drawn completely into femoral socket 60, implant 40 is inserted into hole 71 by drawing on a length of suture 80 or other flexible strand knotted or looped through eye 46, the suture having been pulled through the femur using wire 30, a suture passer, or the like. An impactor chucked into a driver/extractor and having a depth stop 82 can be used to assist in advancing the implant. The implant is advanced in the direction of arrow G. The implant passes under the loop formed in tendons 76, toward the medial side of the femur, to provide cross-pin support of tendons 76.

Figure 14:
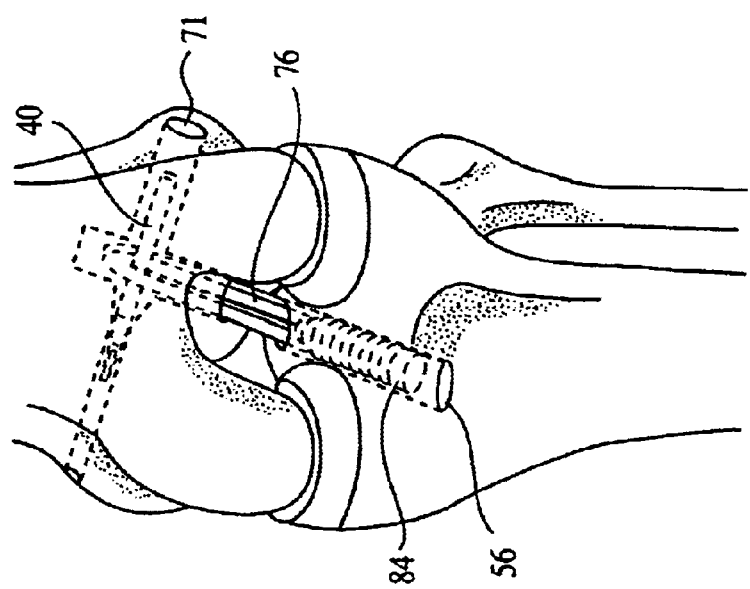
FIG. 14 illustrates a completed tendon graft repair including tibial fixation with an interference screw.

Referring to FIG. 14, the repair is completed by interference fixation of graft 76 in tibial tunnel 56 using interference screw 84. The femoral tunnel is narrow so that tendons 76 fit snugly within tibial tunnel 56 and femoral socket 60, thus avoiding wiping of the tendons along transverse implant 40.

Variations, modifications, and other uses of the present invention will become apparent to those skilled in the art, including the following, non-limiting examples: attachment of bone to bone; attachment of soft tissue to bone; non-medical applications.

Although the present invention has been described in relation to particular embodiments thereof, many other variations and modifications and other uses will become apparent to those skilled in the art. Therefore, the present invention is to be limited not by the specific disclosure herein, but only by the appended claims.

What is claimed is:

1. A method of surgery comprising the steps of:
   forming an opening having side walls in a bone;
   forming a transverse hole through the side walls of the bone;
   inserting a graft having a loop into the opening;
   inserting a flexible strand through an eye formed in a distal end of an implant;

pulling the implant through the transverse hole formed through one of the side walls and into the opening by pulling on the flexible strand; and fixating the graft in the opening by drawing the implant through the loop of the graft by pulling on the flexible strand, such that the implant spans the opening and is supported by the side walls of the bone.

2. The method of claim 1, wherein the implant has a blunt proximal end, and the step of fixating the graft further includes the step of impacting the blunt proximal end of the implant.

3. The method claim 1, wherein the distal end of the implant is tapered.

4. The method of claim 1, wherein the eye of the implant is formed by drilling a hole through the tip of the implant.

5. The method of claim 1, wherein the implant is made entirely of allograft cortical bone.

6. The method of claim 1, wherein the implant is made from a single piece of allograft material.

7. The method of claim 1, wherein a shaft of the implant is cylindrical.

8. The method of claim 1, wherein the flexible strand comprises suture.

9. The method of claim 8, wherein the distal end of the implant includes channels formed on opposite sides of the implant that accommodate the suture to prevent binding of the suture as the implant is inserted into the bone.

10. The method of claim 1, wherein the implant is formed of synthetic bone material.

11. The method of claim 1, wherein the steps of pulling the implant through the transverse hole formed through one of the side walls and drawing the implant through the loop of the graft are performed by attaching the flexible strand to a pin, and pulling the pin through the transverse hole.

12. The method of claim 1, further comprising the step of impacting the implant into said one of the side walls of the bone.

13. The method of claim 1, wherein the bone comprises a femur.

14. A method of anterior cruciate reconstruction surgery of the knee, comprising the steps of:

forming an opening in a femur, the opening having an entrance facing a joint of the knee;

forming a transverse hole through a side wall of the femur and into the opening in the femur;

coupling a graft over to a first flexible strand outside of the knee;

lifting the graft through a tunnel in the tibia and into the opening of the femur by pulling on the first flexible strand; and securing the graft in the opening of the femur by advancing an implant provided with an eye transversely into the opening and under the graft, by pulling on a second flexible stand inserted through the eye of the implant.

15. The method of claim 14, wherein the implant has a blunt proximal end, and the step of fixating the graft further includes the step of impacting the blunt proximal end of the implant.

16. The method of claim 14, wherein die second flexible strand comprises suture.

17. The method of claim 14, wherein the implant has a tapered distal end.

18. The method of claim 16, wherein the distal end of the implant includes channels formed on opposite sides of the implant that accommodate the suture inserted trough the eye of the implant to prevent binding of the suture as the implant is inserted into the bone.

19. The method of claim 14, wherein the eye of the implant is formed by drilling a hole through a tip of the implant.

20. The method of claim 14, wherein the implant is formed of allograft bone.

21. The method claim 14, wherein the implant is formed of synthetic bone material.

22. The method of claim 14, wherein the step of advancing the implant provided with an eye transversely into the opening and under the graft is performed by attaching the second flexible strand to a pin, and pulling the pin through the transverse hole.

* * * * *